United States Patent [19]

Bullard

[11] Patent Number: 5,643,221

[45] Date of Patent: Jul. 1, 1997

[54] CONTROLLED TARGETING LARYNGOSCOPE

[76] Inventor: James Roger Bullard, P.O. Box 14727, Augusta, Ga. 30919-0727

[21] Appl. No.: 287,711

[22] Filed: Aug. 9, 1994

Related U.S. Application Data

[63] Continuation of Ser. No. 780,445, Oct. 17, 1991, abandoned, which is a continuation of Ser. No. 519,440, May 4, 1990, abandoned.

[51] Int. Cl.$^6$ ................................................ A61B 1/267
[52] U.S. Cl. ........................ 604/194; 604/196; 604/188
[58] Field of Search ............................ 128/10, 11, 20, 128/17, 18

[56] References Cited

U.S. PATENT DOCUMENTS

| | | | |
|---|---|---|---|
| Re. 32,306 | 12/1986 | Waters | 04/165 |
| 1,036,000 | 8/1912 | Pease | 128/11 |
| 1,246,338 | 11/1917 | Smit . | |
| 1,613,373 | 1/1927 | Beck . | |
| 1,638,986 | 8/1927 | De Zeng . | |
| 2,354,471 | 7/1944 | Macintosh | 128/10 |
| 2,765,785 | 10/1956 | Pagoto | 128/15 |
| 3,195,536 | 7/1965 | Hovnanian et al. | 128/6 |
| 3,266,059 | 8/1966 | Stelle | 128/4 |
| 3,598,113 | 8/1971 | Moore | 128/11 |
| 3,643,654 | 2/1972 | Felbarg | 128/11 |
| 3,677,262 | 7/1972 | Zukowski | 128/6 |
| 3,727,605 | 4/1973 | Klein | 128/11 |
| 3,766,909 | 10/1973 | Ozbey | 128/11 |
| 3,771,514 | 11/1973 | Huffman et al. | 128/11 |
| 3,776,222 | 12/1973 | Smiddy | 128/6 |
| 3,830,225 | 8/1974 | Shinnick | 128/2 B |
| 3,863,627 | 2/1975 | Bouffard | 128/10 |
| 3,884,222 | 5/1975 | Moore | 128/11 |
| 3,913,568 | 10/1975 | Carpenter | 128/11 |
| 4,063,561 | 12/1977 | McKenna | 128/351 |
| 4,086,919 | 5/1978 | Bullar | 128/11 |
| 4,122,856 | 10/1978 | Mosior et al. | 128/311 |
| 4,329,983 | 5/1982 | Fletcher | 128/207.14 |
| 4,337,761 | 7/1982 | Upsher | 128/11 |
| 4,360,008 | 11/1982 | Corazzelli | 128/11 |
| 4,527,553 | 7/1985 | Upsher | 128/11 |
| 4,573,451 | 3/1986 | Bauman | 128/11 |
| 4,694,826 | 9/1987 | Chester | 128/303 R |
| 4,905,669 | 3/1990 | Bullard et al. | 128/11 |

FOREIGN PATENT DOCUMENTS

| | | | |
|---|---|---|---|
| 1251875A1 | 8/1986 | U.S.S.R. | 128/4 |
| 2133694 | 8/1984 | United Kingdom | 128/20 |

OTHER PUBLICATIONS

"Design Breakthrough In Laryngoscopy" one page Advertisement by J. Roger Bullard, M.D., Oct. 1985.
"Multi-Purpose Anterior Commissure Laryngoscopes" American V. Mueller, . 776.
Reichert Price List, Jul. 1, 1984.
"Fiberscope Cleaning And Disinfection" Advertisement, 1986, available in 128/11 USPTO.

*Primary Examiner*—Mark S. Graham
*Attorney, Agent, or Firm*—Perman & Green

[57] ABSTRACT

A laryngoscope having a rigid shaft, an image bundle, and a movable distal end member connected to the distal end of the shaft. The distal end of the image bundle is located in the distal end member such that the field of view can be changed by moving the distal end member without having to move the rigid shaft. The shaft and distal end member can also have a channel for passing a placement device therethrough such that the positioning of an object at a target area can be controlled by moving the distal end member without having to move the rigid shaft.

11 Claims, 3 Drawing Sheets

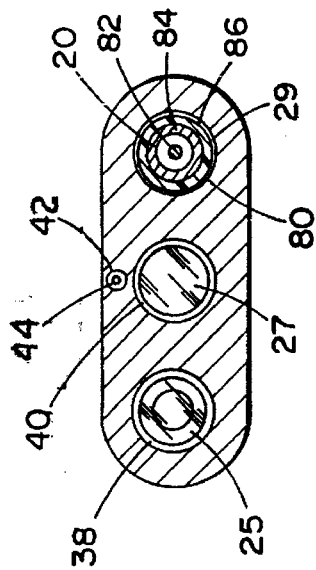
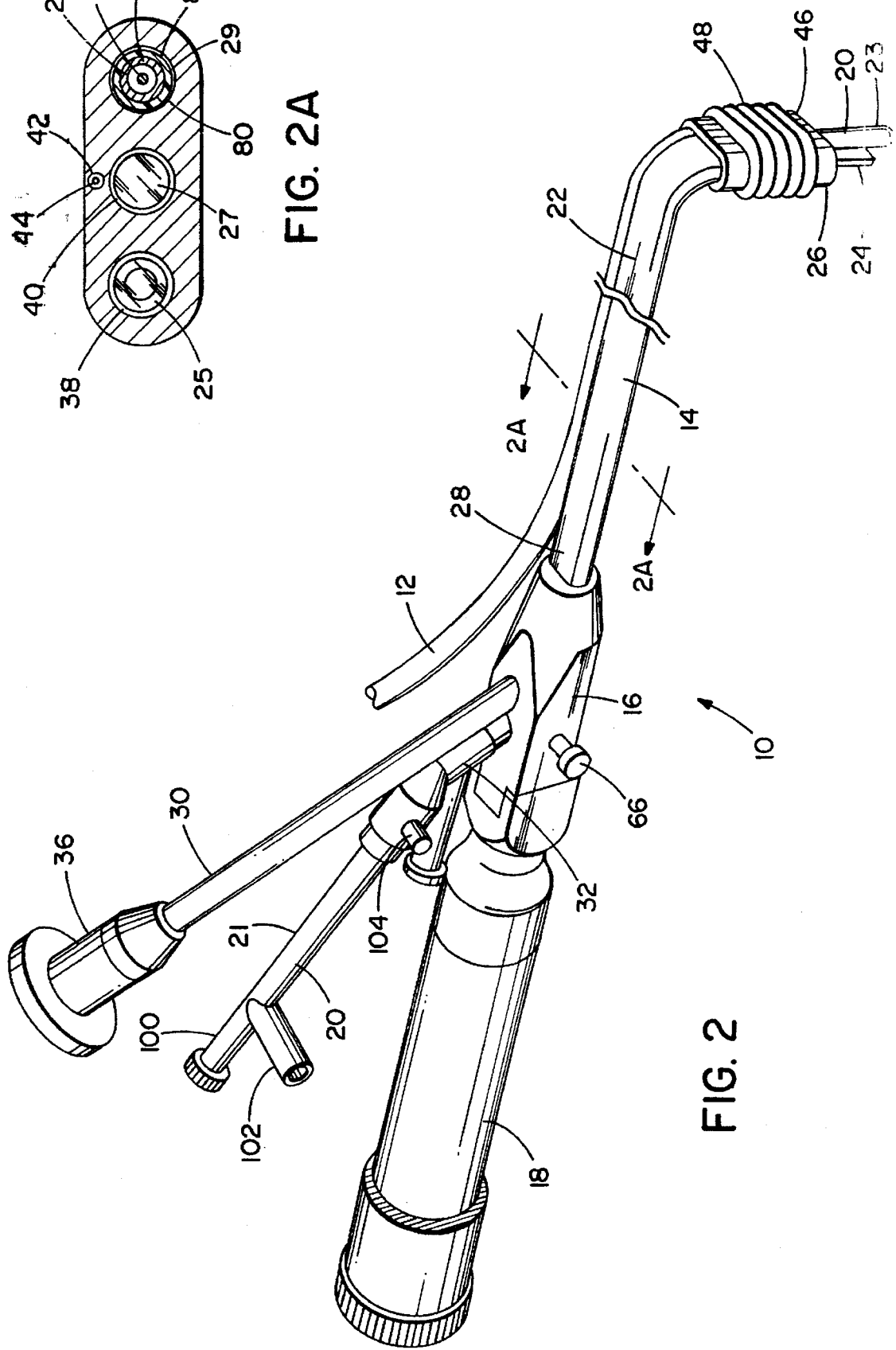

CONTROLLED TARGETING LARYNGOSCOPE

This is a continuation of application Ser. No. 07/780,445 filed on Oct. 17, 1991, abandoned, which is a continuation of Ser. No. 07/519,440 filed on May 4, 1990 abandoned.

BACKGROUND OF THE INVENTION

1. Field of the Invention

The present invention relates to an instrument for accessing a target area of the human body and, more particularly, to an improved instrument having a controllable targeting distal end.

2. Prior Art

Laryngoscopes are widely known and used in the medical field to facilitate endotracheal intubation of a patient during surgery to provide a positive air passageway for the administration of anesthesia and/or for the mechanical ventilation of the lungs of the patient. In the human anatomy, the epiglottis normally overlies the glottis opening into the larynx to prevent the passage of food into the trachea during eating; therefore, in endotracheal intubation, it is necessary to displace the epiglottis from the glottal opening to permit the air tube to be inserted into the trachea.

Various laryngoscope constructions are known. The more widely used laryngoscopes consist of an elongate, rigid metal blade which is supportably attached to a handle and is inserted through the mouth of the patient into the pharyngeal area to displace the tongue and epiglottis and, permit direct visualization of the glottis through the mouth opening. Such laryngoscopes are generally provided with a light source which is directed along the blade to illuminate the area beyond the distal end of the blade. Two general types of rigid blade constructions are the straight, or so called "Miller blade", and the slightly curved, or so called "Macintosh blade." Curved laryngoscope blade constructions having light means to facilitate illumination of the areas of observation are described in U.S. Pat. Nos. 3,598,113; 3,643,654; 3,766,909; and 3,771,514.

The standard method for performing intubation of the trachea during surgery with rigid laryngoscope blades of the straight or slightly curved type is to place the patient in a supine position, tilt the head backwards as far as possible, and distend the lower jaw to widely open the mouth. The rigid blade is then inserted through the mouth into the throat passageway to displace the tongue and epiglottis and expose the glottis of the patient. The larynx is then viewed through the mouth opening from an observation position just above and behind the head of the patient by sighting generally along the axis of the blade. The endotracheal tube is inserted, either orally or transnasally, and passed alongside the blade through the glottis.

Surgical instruments having means for indirect illumination and visualization of the pharyngeal areas of the body are known. U.S. Pat. Nos. 3,776,222 and 3,913,568 disclose devices for endotracheal intubation which comprise flexible or artculatable tubular probes having internal fiber optics for lighting and viewing the internal areas of the body. As disclosed in said patents, the probes carry a slidably removable endotracheal tube surrounding their outer surfaces and the probe is directly inserted into the trachea to position the tube. Such devices obviously require the use of relatively large diameter endotracheal tubes in order to be carried on the tubular probe, and their use necessarily is limited to patients with sufficiently large airway passages to accommodate the combined size of the probe and endotracheal tube. Additionally, due to the flexible nature of the probes, it is difficult to manipulate the probe to displace the tongue and epiglottis to permit direct insertion of the tube into the trachea.

U.S. Pat. No. 2,354,471 by Macintosh discloses a laryngoscope having a handle and hinged blade to facilitate the exposure of the larynx to pass an endotracheal tube. U.S. Pat. No. 3,643,654 by Felbarg discloses a laryngoscope comprised of a tubelike member adapted to be mounted on a conventional handle. U.S. Pat. No. 3,766,909 by Ozbey discloses a laryngoscope with a disposable blade and light guide. U.S. Pat. No. 4,527,553 by Upsher discloses a laryngoscope having a blade and separate handle. U.S. Pat. No. 4,905,669 to Bullard et al. discloses a rigid blade laryngoscope having a movable placement device that can extend from the distal end of the blade to position an intubation tube.

A problem exists with prior art laryngoscopes in that although curved rigid blades are generally effective in visualizing and placing intubation tubes in the larynx of a patient, in certain situations it is not possible to visualize and access a target area such as the glottis without substantial effort and distortion of the patient's internals.

It is a further problem of the prior art that in order to properly visualize a target area the entire rigid blade must be moved.

It is therefore an objective of the present invention to provide a new and improved medical instrument that can overcome the problems in the prior art and provide additional features and advantages.

SUMMARY OF THE INVENTION

The foregoing problems are overcome and other advantages are provided by a medical instrument for visualizing a target area having a rigid blade and a deflectable distal tip.

In accordance with one embodiment of the present invention, a laryngoscope is provided having a frame with a rigid shaft and an image bundle passing therethrough. A distal end member is fixedly connected to the rigid shaft with a portion of the image bundle passing therethrough. The laryngoscope further comprising means for controllably moving the distal end member relative to the rigid shaft, thus moving the distal portion of the image bundle.

In accordance with another embodiment of the present invention an instrument for accessing a target area of a patient is provided comprising an elongate rigid shaft member having at least one channel therein. An image bundle is located, at least partially, in the at least one channel and has a distal end located past a distal end of the shaft member. The instrument further comprises means for moving the image bundle distal end relative to the shaft member such that the shaft member distal end can be relatively stationarily positioned proximate a target area and the image bundle distal end can be moved to visualize a relatively specific area without further moving of the shaft member.

BRIEF DESCRIPTION OF THE DRAWINGS

The foregoing aspects and other features of the invention are explained in the following description, taken in connection with the accompanying drawings, wherein:

FIG. 2 is a perspective view of the laryngoscope as shown in FIG. 1B incorporating features of the present invention.

FIG. 2A is a cross sectional view of the blade of the laryngoscope shown in FIG. 2 taken along line 2A—2A.

DETAILED DESCRIPTION OF THE INVENTION

Figure 1A:
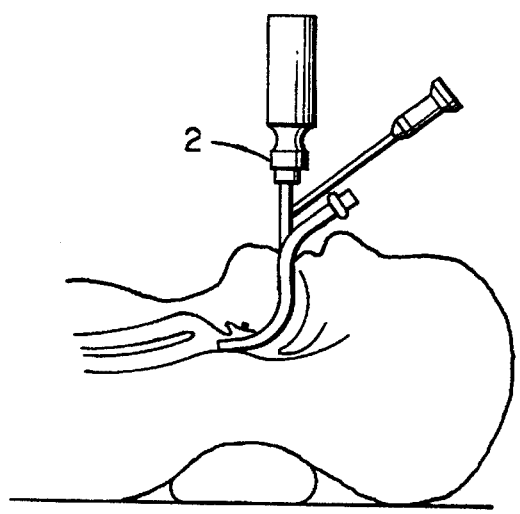
FIG. 1 is an illustrated view of a laryngoscope having a curved rigid blade as in the prior art inserted into a patient.
FIG. 1B is an illustrated view of a laryngoscope incorporating features of the present invention having a substantially rigid blade with a deflectable distal end inserted into a patient.

Referring to FIG. 1A there is shown an illustrated view of a patient in the supine position with a laryngoscope 2 such as that disclosed in U.S. Pat. No. 4,905,669 to Bullard et al. inserted into the patient's mouth. In the event the epiglottis is enlarged or otherwise malformed in such a way that it is not readily displaced from the glottis with the tip inserted into the velecula, the tip or distal end may just as readily be placed directly beneath the epiglottis itself and the blade raised vertically to expose the glottis. The device shown in FIG. 1A is generally for use with various sizes and types of intubation tubes such as cuffed or uncuffed or having an inner diameter of from about 2.5 mm to about 10 mm. However, virtually any size, shape or type of intubation tube can be inserted into a patient.

Although the laryngoscope shown in FIG. 1A is very effective, in certain circumstances, even with a curved blade, it is necessary tilt a patient's head back to obtain access to a patient's glottal opening. In certain circumstances, such as in the event of an upper spinal cord injury, tilting back a patient's head could be very dangerous to the patient. In addition, certain people such as children have such a small and recessed glottal opening that not even a curved blade can allow for fast intubation, even when the head is tilted back. It must also be emphasized that need for a fast intubation may be a life saving event such as in an emergency room situation.

Figure 1B:
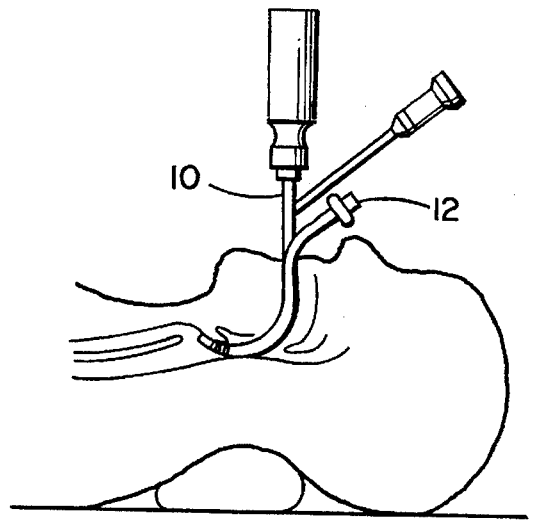

Referring now to FIG. 1B, there is shown an illustrated view of a patient having a laryngoscope 10 incorporating features of the present invention positioned to place an intubation tube 12 into the glottal opening of the patient. Referring also to FIG. 2, a perspective view of the laryngoscope 10 is shown. The laryngoscope 10, in this embodiment, generally comprises a blade section 14, a body section 16 and a removable handle 18. The laryngoscope shown in this embodiment comprises a placement device 20 which can grasp the leading end of the intubation tube 12, move the tube 12 relative to the laryngoscope 10 and release the tube 12 from the placement device 20 at a desired position. A full description of this placement device 20 can be found in U.S. Pat. No. 4,905,669 to Bullard et al. which is incorporated in its entirety by reference herein.

Referring also to FIG. 2A, a cross-sectional view of the blade 14 is shown. In the embodiment shown, the laryngoscope 10 is provided with a fiber optic illumination bundle 25 for illuminating a target area at the distal end 26 of the laryngoscope 10 as well as an image bundle 27 for transmitting an image of an illuminated target area to an eyepiece 36. The handle section 18, in this embodiment, is provided for the operator to securely hold the laryngoscope 10 and control its insertion into the removal from a patient. The handle section 18 also has an interior cavity (not shown) for retaining a power source such as dry cell batteries (not shown). The batteries communicate with a light source (not shown) in the body section 16 which provides light to the fiber optic illumination bundle 25 to illuminate the area adjacent the blade distal end. However, any suitable light source configuration can be used. The handle section 18, in this embodiment, is also disconnectable from the body section 16 for such occasions as cleaning or storage of the instrument 10.

The laryngoscope 10 also comprises an image viewing device 30, in this embodiment, comprising an eye piece 36, optical lenses (not shown) and the fiber optic image bundle 27. The image bundle 27 generally is positioned between the eye piece 36 and the distal end 26 such that an operator can view the area proximate the distal end of the blade section 14 by viewing the image carried by the image bundle at the eye piece 36. However, any suitable image viewing device can be used including a television camera. A secondary working channel entry port 32 is also provided at the body section 16 which communicates with a working channel 29 for transmitting the placement device 20 to the pharyngeal area of the patient.

The blade section 14 of the laryngoscope 10 generally comprises an elongate, rigid shaft or stem 22 and a leaf or petal 24 which can be removable as disclosed in copending Ser. No. 07/192,334 U.S. Pat. No. 4,947,829 filed May 10, 1988. The blade section 14, in this embodiment, has a distal end 26 intended for leading insertion into the patient's mouth and a proximal end 28 supportably connected to the body section 16. The blade section 14, in this embodiment, has a straight configuration with a curved distal end such that a physician can insert the blade section 14 into the mouth of a patient while the patient is in a supine position. However, as will be seen below, the present invention can be used with any type of laryngoscope including laryngoscopes with anatomically curved blades. The shaft 22 generally has four channels passing therethrough; the working channel 29, an illumination bundle channel 38, an image bundle channel 40, and a control channel 42. Passing through the control channel 42 is a control cable 44.

The grasping and extension device 20, in the embodiment shown, comprises a shaft 80 having a connecting member 82, a sheath 84 and a protective cover 86. The connecting member 82 can generally be a compressively stable wire. The wire 82 is generally surrounded by the sheath 84 which increases stability to the shaft but also allows for shaft flexibility and movement of the wire 82 in the sheath 84. The protective cover 86 can be made of any suitable material which allows easy cleaning of the shaft 80 and provides a smooth surface for easy movement of the shaft in the working channel 29.

Located at the distal end of the grasping and extension device 20 is a grasping means 23 comprising a set of single action jaws for grasping a leading portion of the intubation tube 12. A first jaw is relatively stationary with respect to device 20 and is fixed with the sheath 84. A second jaw is pivotally pinned with the device and has the connecting member 82 connected thereto such that the movement of the connecting member 82 relative to the sheath 84 will cause the second jaw to pivot to open and close the jaws. The jaws are generally smooth in profile to prevent damage to tissue during extension and retraction in the patient.

The control 21 in this embodiment, generally controls at least two functions of the grasping and extension device 20.

First, the control 21 can control the movement of device in the working channel 29 of the blade. Second, the control 21 can control the operation of the grasping means 23 at the distal end of the device. In the embodiment shown in FIG. 2, the control 21 can control the movement of the second jaw.

The control 21 shown in FIG. 2 generally comprises a relatively stationary contact sleeve or hub, a shaft stop sleeve or flange, a grasping biasing spring, a push block, a stationary slide tube 100 and a control lever 102. The contact sleeve has a central aperture being sized to accommodate the shaft and allow movement therethrough. The sleeve has a keying lock 104 for stationary yet removable positioning of the control on the control head 16. The lock 104 has a detent with a central aperture for passage of the shaft in both its compressed and extended positions. The sleeve can be mounted to a first end of the slide tube 100 and has an interior face for contacting the stop sleeve.

In a first or home position, the control lever 102 is in a fully retracted position with the proximal end of the connecting member 82, the proximal end of the sheath 84 and cover 86 being in a retracted position with the jaws biased in a closed position. With the control 21 and grasping and extending device 20 mounted with the laryngoscope 10 as shown in FIG. 2, the lock 104 mounts the control 21 onto the control head 16 with the shaft 80 passing through the control head 16 into the working channel 29 in the blade and the grasping means 23 being located proximate the distal end of the blade.

Figure 3A:
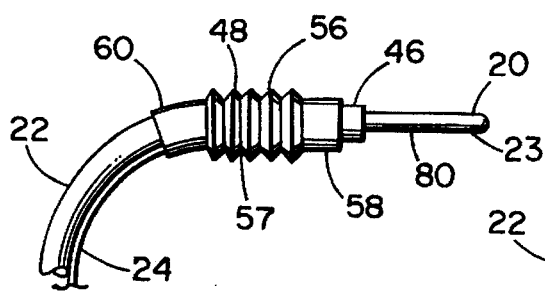
FIG. 3A is a partial plan view of the distal end of the laryngoscope shown in FIG. 2 with its distal tip at a home position.

The operator, by pushing on the control lever 102 can move the push block, biasing spring, stop sleeve and shaft 80 along the interior cavity of the slide tube 100 to a second extended position. The guide slot and screw cooperate to keep the control 21 and device 20 oriented in a relatively constant position. In the second position, the stop sleeve contacts the contact sleeve. However, the biasing spring has not been additionally compressed. Thus, the jaws remain biased in a closed position as the control moves between the first and second position. As the control has been moved, the entire grasping and extending device 20 has moved relative to the laryngoscope. The shaft 80 has longitudinally moved along the working channel 29 of the blade. The grasping means 23 has also moved from a first position proximate the blade distal end to a second position which is extended from the blade distal end as illustrated in FIG. 3A. In a preferred embodiment the second position is from about ¾ inch to about 1½ inches from the first position. However, any desired amount of travel can be accommodated.

At a third jaws opening position, the distal end of the device 20 remains stationary relative to the laryngoscope at the second extended position. However, the operator, by pushing on the control lever 102 has moved the push block relative to the stop sleeve and compressed the spring. The connecting member 82 pushes on the second jaw which causes the jaw to move about the pivot thereby opening the second jaw relative to the first jaw. When the jaws are open, the intubation tube 12 can be released from the device 20.

The use of this particular embodiment will be described in inserting an intubation tube into the trachea region of a patient in which the region is easily viewed. Before insertion of the laryngoscope and tube into the patient, the operator will extend the device to the second extended position and open the jaws. The operator can then attach the intubation tube to the device. In a preferred method of attaching the leading portion of a tube 12 to the device 20, the jaws grasp the tube proximate a Murphy eye in the tube. However, any suitable grasping or connecting means could be used to attach or connect the tube with the grasping and extending device.

After the tube 12 has been grasped, the device 20 is retracted to the first or home position. The operator can then insert the blade and tube into the mouth and throat of the patient as diagrammatically illustrated in FIG. 1A. Once the blade has been fully inserted, the operator should be able to view the target area, in this case the glottis or vocal cords. The operator can now position the tube through the glottis. At the home position, the operator can view both the target area and a leading portion of the tube. The operator can move the control lever forward thereby extending the device 20 towards the second extended position. The grasping and extending device 20 is urged through the working channel 29 of the blade and advances the grasping means and leading edge of the tube towards the target area. Preferably, the vocal cords have been relaxed via a muscle relaxant to widen the opening. The control head and blade of the laryngoscope remains stationary as the device 20 and tube 12 are urged forward and the operator's field of view remains relatively constant. The operator can, if necessary move the laryngoscope to adjust the eventual positioning of the tube or passage through the glottis.

Once the leading portion of the tube has been properly positioned, the operator can release the tube from the grasping means. The second jaw is capable of pivoting about 90 degrees to allow the tube 12 and grasping and extending device 20 to become separated. Preferably, a cuffed intubation tube is used. When the leading edge of the tube is properly positioned, the cuffed section of the tube is expanded to fixedly position the leading edge of the tube between the vocal cords and the branching of the main bronchi. The grasping and extending device 20 can then be removed. If an uncuffed tube is used the grasping and extending device 20 and the tube 12 can be separated by the operator simply by holding the tube proximate the patients mouth and withdrawing the grasping and extending device 20 from the tube 12. The positioning of the tube 12 can of course be checked and adjusted as known in the art. After placement of the tube, or at least the leading portion of the tube, the operator can then remove the laryngoscope from the patient. The present invention thus allows for a fast, precise and individualized access to the larynx and trachea region of a patient and placement of the tube in the trachea when the target area is easily visible. The use of the laryngoscope 10 when the target area is not easily visible will be described below.

Figure 3B:
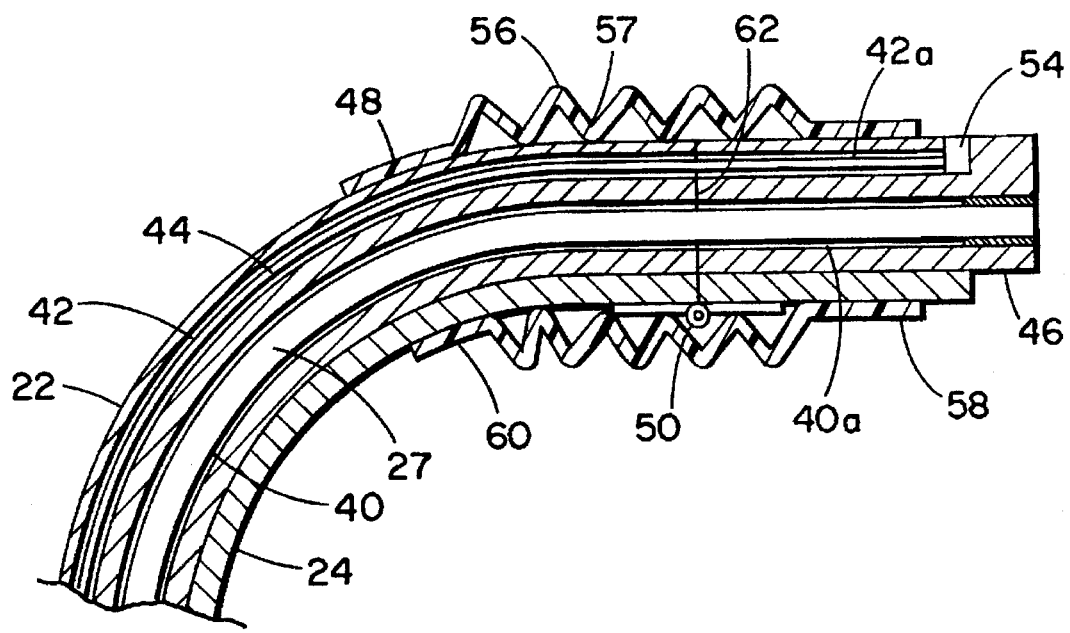
FIG. 3B is an enlarged cross sectional view of the distal end shown in FIG. 3A.

Referring also to FIGS. 3A and 3B, the blade 14, in the embodiment shown, also comprises a distal end member 46 and a flexible cover 48. The distal end member 46, in the embodiment shown, is a rigid member having four channels substantially identical to the channels 29, 38, 40, 42 in the shaft 22. In the embodiment shown, the blade 24 has a hinge 50 that fixedly, but pivotally connects the distal end of the shaft 22 to the distal end member 46. In an alternate embodiment of the invention the shaft 22 and distal end member 46 may be directly movably connected to each other and, although a hinged connection is disclosed, any suitable type of movable connection may be provided. The image bundle 27 extends past the distal end of the shaft 22 into channel 40a and is fixed therein. The control cable 44 also extends past the distal end of the shaft 22 into channel 42a and is fixed therein by a connector 54. The hinge 50 is mounted on the inner surface of the blade 14.

The cover 48 is generally comprised of a flexible resilient material such as a polymer and has a general tubular shape with corrugated type ridges 56 and valleys 57 between a first end 58 and a second end 60. The cover or boot 48 is generally provided to cover or seal off the junction 62 between the distal end of the shaft 22 and the distal end member 46. The first end 58 of the cover 48 fits snugly over the outside of the distal end member 46. The second end 60 fits snugly over the shaft 22. The corrugations in the cover 48 are generally provided to allow the distal end member to move relative to the shaft 22 while keeping the cover ends 58 and 60 snugly fitted to the distal end member 46 and shaft 22. Although the cover 48 is shown in this embodiment as covering the leaf 24, in an alternate embodiment, the leaf 24 need not be located in the cover 48. In addition, the bottom of the cover 48 need not be corrugated so long as the top of the cover 48 is flexible.

Figure 4A:
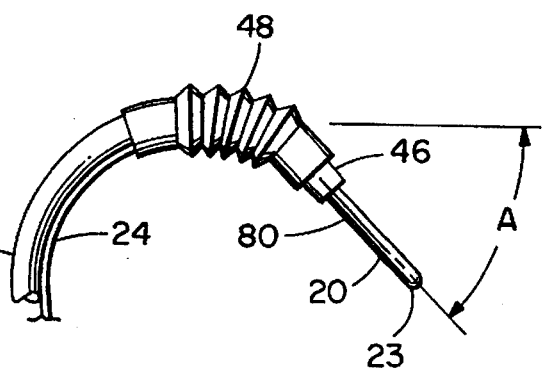
FIG. 4A is a plan view of the distal end shown in FIG. 3A at a deflected position.
Figure 5:
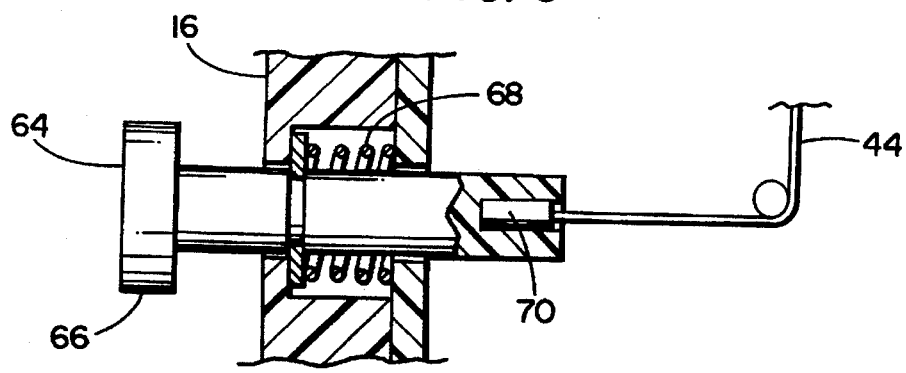
FIG. 5 is a partial cross-sectional view of a control for deflection of the laryngoscope distal end.
Figure 4B:
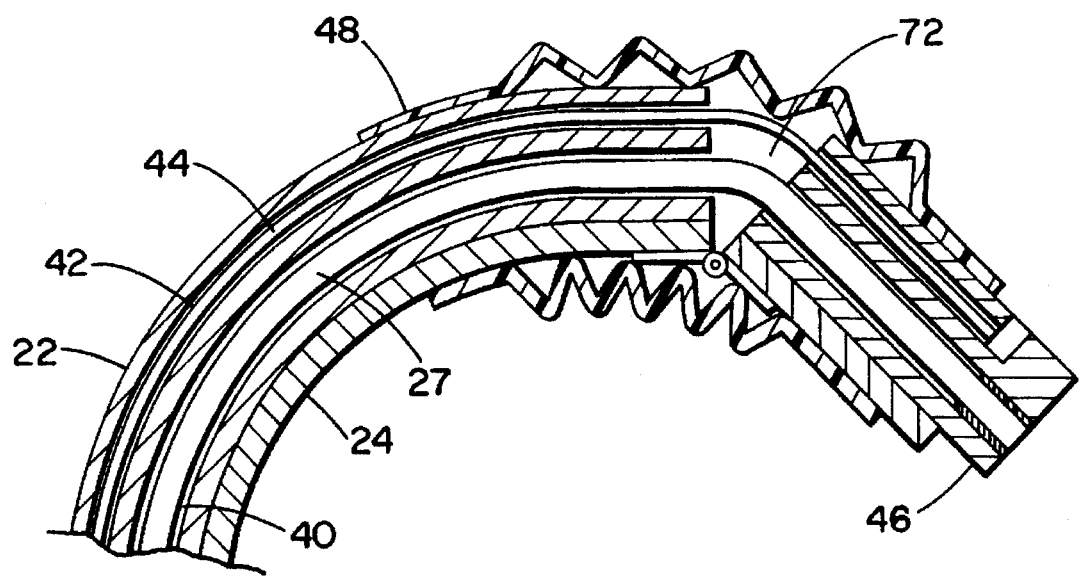
FIG. 4B is an enlarged cross-sectional view of the distal end shown in FIG. 4A.

Referring now also to FIGS. 4A, 4B and 5, the control cable 44, in the embodiment shown, is connected at its distal end to the distal end member 46 via the connector 54 for pushing and pulling the distal end member 46 at a location offset from the hinge 50 to thereby move the distal end member 46 from its home position shown in FIG. 3A to a deflected or pivoted position as shown in FIG. 4A and back again. The cable 44 is movable in the control channel 42 and has its proximal end connected to deflection control 64 in the body section 16. In the embodiment shown, the deflection control 64 generally comprises a depressible button 66, a biasing spring 68, and a connector 70. The connector 70 connects the proximal end of the cable 44 to the button 66. The spring 68 biases the button 66 in the outward position thus pulling on the cable 44. This in turn keeps the distal end member 46 in its home position. When the button 66 is depressed by an operator the cable 44 is pushed forward to push on the distal end member 46 and deflect it as shown in FIGS. 4A and 4B. Although only one type of deflection control is described above, it should be understood that any suitable type of deflection control can be used.

When the button 66 is depressed the cable 44 pivots the distal end member away from the distal end of the shaft 22. The presence of the cover 48 keeps a gap 72 formed at the junction 62 isolated inside the laryngoscope. The cable 44 has sufficient rigidity so as not to collapse while pushing the distal end member 46. The illumination bundle 25, image bundle 27, and placement device 20 are sufficiently flexible to bend and traverse the gap 72. Suitable means (not shown) are provided in the body section 16 to compensate for the extension of length of the two bundles 25 and 27 when the distal end member 46 is deflected.

In the embodiment shown, the distal end member 46 has an angle of deflection A of about 45 degrees in an inward direction. However, any suitable angle of deflection A can be provided including up to 90 degrees. In addition, suitable means may be provided to deflect the distal end member 46 in other than an inward direction as shown. In the embodiment shown, the length of travel of the cable 44 limits the amount of deflection of the distal end member 46. However, any suitable type of deflection limiter can be provided. When the operator releases the button 66, the spring 68 of the control 64 pushes the button 66 back to its extended position. The button 66, in turn, pulls on the cable 44 which pulls on the distal end member 46. This returns the distal end member 46 back to its home position.

For using the laryngoscope 10, an operator will first position the shaft 22 in a patient's mouth with the distal end of the laryngoscope being located proximate the patient's glottis opening. With the glottis opening visualized, the operator can use the placement device 20 to position an intubation tube and, the laryngoscope 10 is then removed. In the event that the operator is unable to visualize the glottis opening of the patient and, moving the patient's head to open a visual path either cannot be done or could injure the patient, the operator can depress the button 66 to deflect the distal end member 46 to gain visual sight of the glottis opening and, thus advance the placement device 20 at a new angle to quickly place an intubation tube in the glottis opening. Hence, when the glottis opening is easily viewed, the distal end member 46 need not be moved from its home position. On the other hand, when the glottis opening is not easily viewed, the operator can angle the distal end member 46 to view the glottis opening and by advancing the placement device 20, directs the intubation tube 12 to the glottis opening without having to move the rest of the laryngoscope.

The present invention can thus function as both a standard rigid blade laryngoscope with placement device which can interact and displace the epiglottis and also, act as partially flexible laryngoscope depending upon the operators needs for a particular patient. This allows for a relatively quick intubation in virtually all circumstances. Although the present invention has been described as a laryngoscope, it should be understood that the present invention can be used in any suitable type of visualization instrument that requires a ridge structure to interact with portions of the human body and also have a deflectable distal end that can change the angle of visualization or angle of attack for moving an object to a target area. One particular alternate device that the present invention could be used in could be a device for visualizing the upper throat region of a patient in the supine position wherein the device could have a 90 degree deflectable end and also be mounted to an apparatus for rotating the device 360 degrees such as for use by ear, throat and nose specialists. However, as noted above, the present invention can be used in any suitable medical apparatus.

It should be understood that the foregoing description is only illustrative of the invention. Various alternatives and modifications can be devised by those skilled in the art without departing from the scope of the invention. Accordingly, the present invention is intended to embrace all such alternatives, modifications and variances which fall within the scope of the appended claims.

What is claimed is:

1. A laryngoscope comprising:
   a frame having a body section and a rigid shaft extending from the body section, the shaft being adapted to move a patient's tongue and having an image bundle passing therethrough;
   a distal end member pivotally attached to the rigid shaft with a portion of the image bundle passing therethrough;
   an intubation tube installation device extending through channels in the shaft and distal end member, the device having a front end that is extendable from a front end of the distal end member; and
   means for adjusting an angle of extension of the front end of the installation device from the shaft without moving the shaft.

2. A laryngoscope as in claim 1 further comprising a resilient flexible cover covering a junction between said shaft and said distal end member.

3. A laryngoscope as in claim 2 wherein said cover has a corrugation type tubular shape.

4. A laryngoscope as in claim 1 wherein said distal end member has an angle of pivot of about 45 degrees in single direction from a home position that is aligned with the shaft.

5. A laryngoscope as in claim 1 wherein said means for adjusting moves said distal end member and comprises a cable like member capable of pushing and pulling said end member.

6. A laryngoscope as in claim 1 further comprising means for biasing said distal end member at a home position with the distal end member located flush against an end of the shaft.

7. A laryngoscope as in claim 1 further comprising an illumination bundle passing through illumination channels in the shaft and distal end member.

8. A laryngoscope comprising:

a frame having a body section and a rigid shaft extending from the body section, the shaft being adapted to move a patient's tongue and including at least three shaft channels passing therethrough;

a distal end member directly movably attached to a front end of the shaft, the distal end member having at least three distal end channels therethrough;

a fiber optic illumination member located in a first one of the shaft channels and a first one of the distal end channels;

a fiber optic image member located in a second one of the shaft channels and a second one of the distal end channels; and means for moving ends of the fiber optic illumination member and fiber optic image member located in the distal end member relative to the shaft.

9. A laryngoscope as in claim 8 wherein the means for moving includes a cable located in a third one of the shaft channels and a third one of the distal end channels.

10. A laryngoscope as in claim 8 further comprising an intubation tube installation device movably located in a third one of the shaft channels and a third one of the distal end channels.

11. A laryngoscope as in claim 10 wherein a front end of the installation device is extendable in a forward direction from a front end of the distal end member and, an angle of extension of the installation device relative to the shaft is changed when the distal end member is moved relative to the shaft.

* * * * *